United States Patent [19]
Sjoholm

[11] Patent Number: 6,032,067
[45] Date of Patent: Feb. 29, 2000

[54] RADIATION DELIVERY SYSTEM

[75] Inventor: Gosta Sjoholm, Bromma, Sweden

[73] Assignee: Siemens Elema AB, Solna, Sweden

[21] Appl. No.: 09/161,654

[22] Filed: Sep. 28, 1998

[30] Foreign Application Priority Data

Sep. 30, 1997 [SE] Sweden .................................. 9703543

[51] Int. Cl.[7] .................................. A61B 5/00; A61B 8/00
[52] U.S. Cl. ........................................... 600/407; 600/439
[58] Field of Search .................................... 600/439, 443, 600/462, 459, 407, 411; 607/122, 125; 601/3, 2; 128/898, 899

[56] References Cited

U.S. PATENT DOCUMENTS

| | | | |
|---|---|---|---|
| 5,383,466 | 1/1995 | Partika | 128/662.03 |
| 5,590,657 | 1/1997 | Cain et al. | 128/660.03 |
| 5,624,382 | 4/1997 | Oppelt et al. | 600/439 X |
| 5,817,021 | 10/1998 | Reichenberger | 600/439 |
| 5,840,030 | 11/1998 | Ferek-Petric et al. | 600/439 |
| 5,899,857 | 5/1999 | Wilk | 600/411 X |
| 5,938,600 | 8/1999 | Von Voals et al. | 600/411 |

*Primary Examiner*—Francis J. Jaworski
*Attorney, Agent, or Firm*—Hill & Simpson

[57] ABSTRACT

A system for delivering radiation to an intracorporeal target site has a controllable external radiation source 8 and a cooperable location system for controlling the radiation source to deliver radiation to the internal target site. The location system includes a reference element positionable at an internal site having a known spatial relationship with the target site, this element being configured to provide an output signal related to its location for controlling the radiation source.

9 Claims, 2 Drawing Sheets

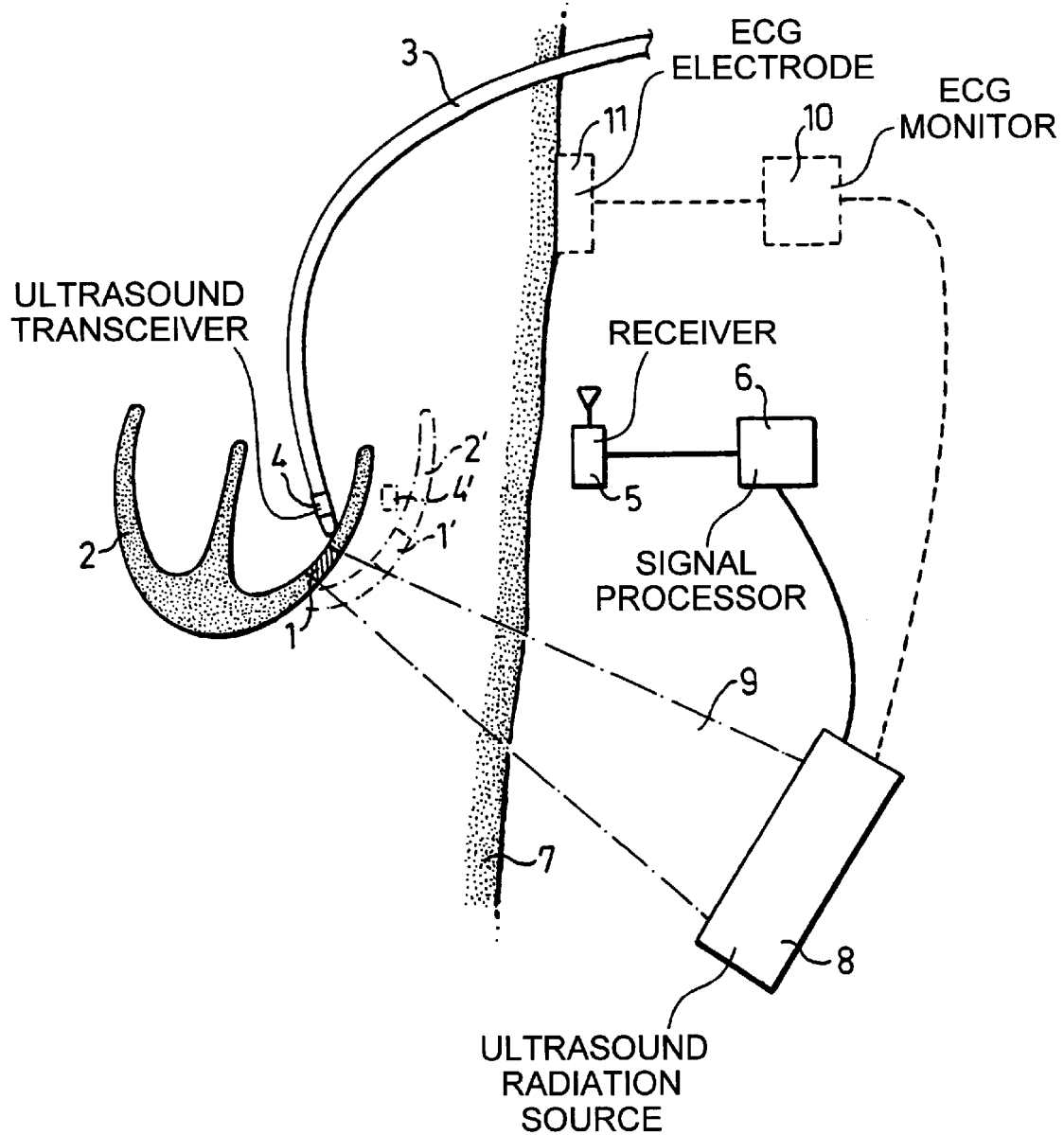

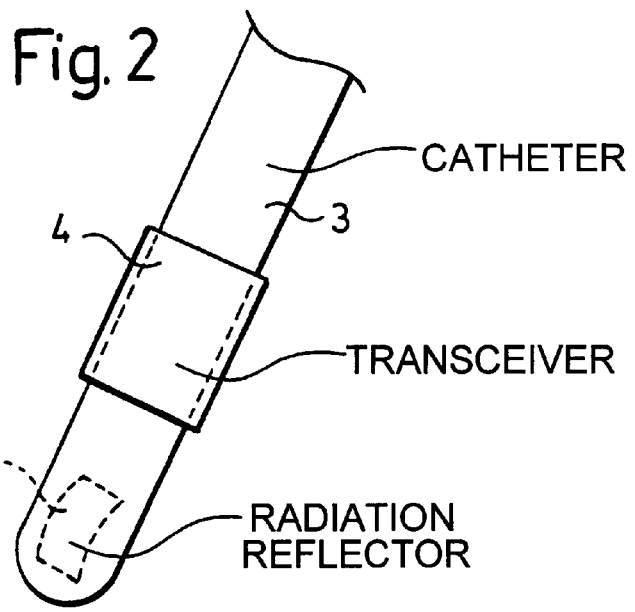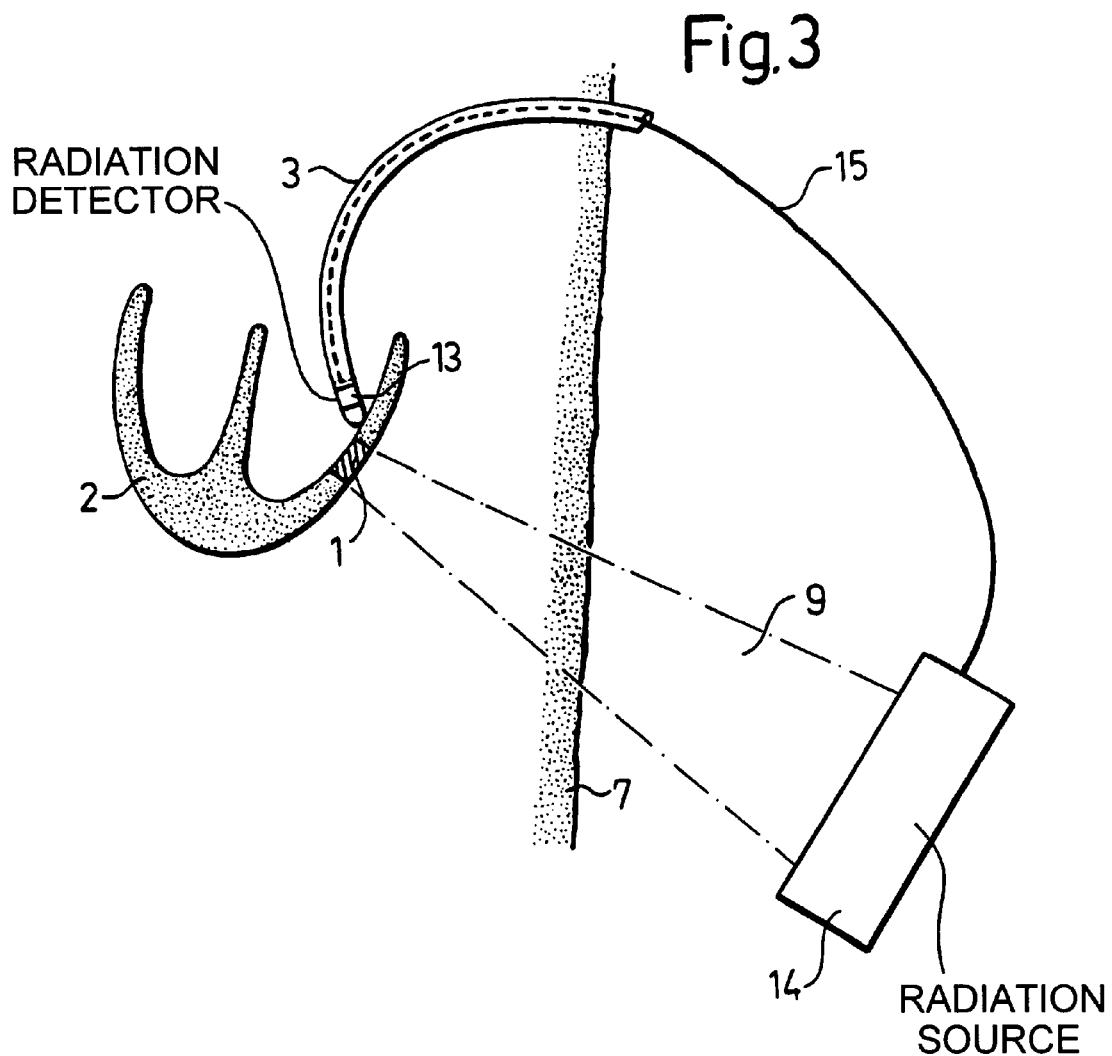

RADIATION DELIVERY SYSTEM

BACKGROUND OF THE INVENTION

1. Field of the Invention

The present invention relates to a radiation delivery system, and in particular to a radiation delivery system used in the non-invasive treatment of human body tissue.

2. Description of the Prior Art

Systems which employ an external radiation source to modify internal body tissue are well known. Examples of such systems include radiotherapy systems, in which an external source delivers nuclear radiation to the body for example to destroy tumors; and ultrasound systems, in which an external source delivers ultrasound to the body for example to destroy kidney stones.

Problems with such systems are that it is often difficult to accurately locate an internal target site which is to receive the radiation and that it is sometimes difficult to maintain delivery of the radiation to that site. These problems may be particularly acute when the site itself is cont inuously moving relative to the body and to the radiation source. This can occur when the site is located on a moving organ such as the heart. In order for the physician to be sure that the internal target site receives a useful dose of radiation an area of tissue much larger than the site itself often may be irradiated. This can result in unnecessary damage to healthy tissue.

A further problem is that any unexpected movement of the body may result in the target site receiving less than the expected dose of radiation.

One known device which attempts to address at least some of these problems is described in the European Patent 0 400 196. This document discloses a radiation delivery system in which an ultrasound source is linked to an X-ray device. The X-ray device is used to locate the target site within the body and to provide information to control the delivery of ultrasound to that site. At least two X-ray images are required each time 3-dimensional position information is needed. Thus both the physician and the patient may be exposed to potentially hazardous ionizing radiation. This may be particularly problematical if the system were to be employed to monitor a movable target site as this is likely to require a large number of X-ray images to be made during a single procedure.

SUMMARY OF THE INVENTION

It is an object of the present invention to provide a radiation delivery system in which at least some of the aforementioned problems associated with the known radiation delivery systems are reduced.

The above object is achieved in accordance with the principles of the present invention in a system for delivering radiation to an intracorporeal target including a controllable extracorporeal radiation source and a locating system for controlling the radiation source to deliver radiation to the target site, the locating system including a reference element positionable at an intracorporeal site having a known spatial relationship with the target site, the reference element being configured to provide an output signal related to its location for use in controlling the radiation source.

Thus the radiation source, which may be formed as an array of radiation supplies operable in a group or separately, can be automatically controlled, for example by moving the focus of the source or by varying the level of radiation from the source, to deliver radiation to a target site and so minimize the destructive irradiation of tissue surrounding the target site.

Moreover, the use of an internal reference element which can be positioned at or near the target site means that the reference element can move as the target site moves. This allows the radiation source to track the movement of the target site so that the risk of damaging healthy tissue is further reduced.

The radiation delivery system according to the present invention may also include an element, positionable within the body, for modifying the path of the radiation within the body. This provides a greater control over the delivery of radiation to the target site. For example, a defocusing reflector may be used, perhaps mounted on or in the reference element, to reflect radiation from the radiation source over an area larger than that of the incident beam.

Simply, the reference element of the location system may include a radiation detector which provides an output dependent on the presence of radiation from the radiation source. The detector can be advantageously arranged to provide an output signal directly proportional to the level of detected radiation. In this way the radiation source may be controlled to more accurately deliver radiation to the target site than if the detector detected only the presence or absence of incident radiation.

The location system may additionally or alternatively include a non-ionizing radiation transmitter and receiver elements cooperating therewith to sense the position in space of a reference element which includes either the transmitter or receiver element. An output signal dependent on the sensed position of the reference element may then be generated to control the radiation source. This has an advantage that harmful radiation need not be present until the radiation source is focused on the target site.

Location systems that can sense the position of catheters within a body by using non-ionizing radiation are well known in the art. Examples of such systems are described in U.S. Pat. Nos. 5,042,486 and 5,391,199, both of which describe systems which employ electromagnetic or ultrasound radiation to track a catheter, and in PCT Application WO 95/09562, which describes a system for tracking a catheter using a magnetic field. All such systems work by equipping the catheter to be tracked with a radiation receiver or transmitter and having a complementary transmitter or receiver positioned outside the body. Radiation received from the transmitter can then be analyzed to provide information on the position of the catheter within the body. This information may then be used by a physician to guide a so called "minimally invasive medical tool", such as an ablation catheter, a mapping catheter or an endoscope through the body to a target site where surgical treatment is to be carried out.

In contrast to these known systems, the use in the inventive location system of a reference element which combines both a detector to detect radiation from the radiation source and also a position sensor allows the output from both the detector and sensor to be employed to control the radiation source. In this way there may be a greater certainty that the target site will be irradiated.

In such a system the radiation from the radiation source and the non-ionizing radiation used to sense position may both be ultrasound, perhaps of different frequencies to assist in the identification of their origin. This has the advantage that the reference means may be simplified in ways common in the art so that the device used in sensing the position of the reference element is also used to detect incident radiation from the radiation source.

DESCRIPTION OF THE DRAWINGS

FIG. 1 shows a schematic representation of a first system embodiment according to the present invention.

FIG. 2 shows a schematic representation of the tip of a reference catheter usable in the system of FIG. 1.

FIG. 3 shows a schematic representation of a second system embodiment according to the present invention.

DESCRIPTION OF THE PREFERRED EMBODIMENTS

Referring to FIG. 1, a target site 1 is situated within the heart 2. A location system includes an internal reference catheter 3 having an ultrasound transceiver 4 disposed proximate its tip; a cooperable receiver 5 and a signal processor 6, which may be a suitably programmed computer. The location system provides to the cooperable ultrasound radiation source 8 an output signal dependent on the sensed position of the transceiver 4. The transceiver 4 is configured to serially operate both as a transmitter, to provide a location signal for the receiver 5, and as a receiver, to provide an output signal proportional to the level of radiation received from the radiation source 8.

The transceiver 4 of the catheter 3 is positioned at a known distance from the target site 1 to move as the target site 1 moves, for example as the heart 2 beats (shown as 1', 2' and 4'). This arrangement can then be used to locate the target site 1 at any time in the cardiac cycle. The accurate positioning of the catheter 3 within the heart 2 can be done using the location system 4, 5, 6 in a manner known in the art, for example as described in U.S. Pat. No. 5,042,486.

In use, the signal processor 6 receives a signal from the receiver 5 which is dependent on the relative positions of the transceiver 4 and the receiver 5 and analyzes the signal to sense the position of the transceiver 4 within the body 7. The processor 6 then provides a control signal to the external radiation source 8 dependent on this sensed position. The radiation source 8 is provided with control means, responsive to the control signal, to control the movement of the incident radiation beam 9 in order to maintain focus on the target site 1 as the heart 2 beats.

Alternatively, the focus of the beam 9 can remain fixed and the control signal can be employed to switch the beam 9 on and off as the target site 1 passes through the beam 9 during a heart beat.

In a modification to this embodiment the output of a cardiac monitor, such as an ECG system, (shown in broken lines and composed of an ECG electrode 11 and an ECG monitor 10 is also used to control the output of the radiation source 8. This additional control signal can ensure that irradiation occurs at a known point in every cardiac cycle. Here the location system 4, 5, 6 may be used to move the focus of the beam to a predetermined position in which the target site 1 will be irradiated by the beam 9 for at least a part of the cardiac cycle. Once positioned the operation of the radiation source 8 is determined by the output of the cardiac monitor 10, 11 so that the beam 9 is on only for some or all of that part of the cardiac cycle in which the target site 1 lies within the beam 9.

Before the site is irradiated the radiation delivery system may be calibrated in order to correlate the position of the heart 2 with the output from the cardiac monitor 10, 11. The location system may be used for this purpose by arranging for the position of the transceiver 4 to be sensed at known points in the cardiac cycle (determined using the cardiac monitor 10, 11). Once this correlation has been determined then the part of the cardiac cycle during which the target site 1 will lie within the beam 9 can be calculated and the output from the cardiac monitor 10,11 used to switch the beam 9 on and off as appropriate. The transceiver 4, operating as a receiver, can be used to provide an output signal dependent on the level of incident radiation from the beam 9. This signal can be used as a safety precaution so that the beam 9 is switched to maximum intensity only when there is an output signal from the transceiver 4.

A portion of a catheter 3, which may be used in the above described system, is shown in FIG. 2. A cylindrical transceiver 4 is positioned about the catheter 3 and proximal its tip. A curved radiation reflector 12 is positioned inside the catheter 3, between its tip and the transceiver 4. This reflector is curved so as to be able to defocus and reflect incident radiation 9 from the source 8 towards the target site 1.

A further embodiment of a system according to the present invention is shown in FIG. 3 in which items similar to those in FIG. 1 have the same reference numerals.

In FIG. 3 the target site 1 is again within the heart 2 and a catheter 3 is provided having proximal its tip a nuclear radiation detector 13. The detector 13 is adapted to provide an output signal proportional to the intensity of incident radiation from a nuclear radiation source 14. Conveniently the output signal is in the form of an electric current which passes through a wire 15 within the catheter 3 to the radiation source 14 to control the intensity of the beam 9.

In use, the output of the beam 9 is arranged to have a default intensity which is less than that to be used to irradiate the target site 1. As the output signal from the detector 13 increases above a predetermined level, for example as the focus of the source 14 is manually moved toward the target site or as the target site 1 passes through the beam when the heart 2 beats, the intensity of the beam 9 is increased to its treatment level. As the output from the detector 13 decreases below the same or a different predetermined level the intensity of the beam 9 is reduced to its default level. In this way the radiation induced damage to healthy tissue which surrounds the target site 1 can be reduced.

It will be apparent to those skilled in the art that other combinations of radiation detector, position sensor, cardiac monitor or other monitor may be employed or that the analysis of signals and the control of the radiation source may be done by using a separate, suitably programmed computer or by using dedicated hardware which may be located within any monitor or the radiation source of the delivery system while remaining within the scope of the invention as claimed.

Although modifications and changes may be suggested by those skilled in the art, it is the intention of the inventor to embody within the patent warranted hereon all changes and modifications as reasonably and properly come within the scope of his contribution to the art.

I claim as my invention:

1. A system for delivering radiation to an intracorporeal target site, comprising:

a controllable radiation source for generating a radiation beam for delivery to an intracorporeal target site which exhibits rapid periodic physiological movement;

a control unit connected to the radiation source to control at least movement of the beam dependent on a control signal; and a locating system comprising an extracorporeal non-ionizing radiation transmitter or receiver; a reference element comprising a complementary receiver or transmitter positionable at an intracorporeal site having a known spatial relationship to the target site and which also exhibits said rapid physiological movement; and a signal processor for identifying when a signal transmitted by the radiation transmitter and received by the complementary radiation receiver is present, the presence of said signal being sufficient in said signal processor to locate the intracorporeal position of the reference element, and said signal processor providing an output signal representative of the position of the reference element for use as the control signal.

2. A system as claimed in claim 1 wherein said reference element comprises said non-ionizing radiation transmitter.

3. A system as claimed in claim 1 wherein said reference element comprises said receiver.

4. A system as claimed in claim 1 wherein said reference element comprises a minimally invasive medical instrument.

5. A system as claimed in claim 4 wherein said minimally invasive medical instrument comprises a catheter having a portion shaped to modify a path of incident radiation from said radiation source to direct said incident radiation to said target site.

6. A system as claimed in claim 5 wherein said portion of said catheter comprises a defocusing radiation reflector.

7. A system as claimed in claim 1 wherein said radiation source has a focus, and wherein said locating system comprises means for controlling a position of said focus of said radiation source dependent on said output signal from said reference element.

8. A system as claimed in claim 1 wherein said radiation source emits radiation at an intensity, and wherein said locating system comprises means for varying said intensity of said radiation dependent on said output signal.

9. A system as claimed in claim 1 further comprising a cardiac function monitor connected for interaction with said radiation source to synchronize operation of said radiation source with a predetermined phase in a cardiac cycle.

* * * * *